United States Patent [19]
McKeating

[11] Patent Number: 5,746,747
[45] Date of Patent: May 5, 1998

[54] POLYPECTOMY INSTRUMENT

[76] Inventor: John A. McKeating, 1074 Osage Dr., Pittsburgh, Pa. 15235

[21] Appl. No.: 242,178

[22] Filed: May 13, 1994

[51] Int. Cl.$^6$ .................................................. A61B 17/24
[52] U.S. Cl. .............................. 606/114; 606/113; 606/110
[58] Field of Search ............................. 606/1, 110, 113, 606/114, 127, 128, 27, 32, 37, 39, 40, 45–50

[56] References Cited

U.S. PATENT DOCUMENTS

| | | | |
|---|---|---|---|
| 5,201,740 | 4/1993 | Nakao et al. | 606/113 |
| 5,201,741 | 4/1993 | Dulebohn | 606/110 |
| 5,290,294 | 3/1994 | Cox et al. | 606/205 |
| 5,312,391 | 5/1994 | Wilk | 606/205 |
| 5,336,227 | 8/1994 | Nakao et al. | 606/113 |
| 5,417,697 | 5/1995 | Wilk et al. | 606/113 |

*Primary Examiner*—Glenn Dawson
*Attorney, Agent, or Firm*—Ansel M. Schwartz

[57] ABSTRACT

An instrument to perform endoscopic polypectomy having a first portion which grasps a polyp and a second portion which cuts away the polyps. The second portion is in contact with the first portion while the first portion grasps the polyp when the polyp is cut by the second portion. The first sheath member preferably contains a small grasping forcep mechanism. The second sheath member preferably contains a wire snare mechanism.

6 Claims, 2 Drawing Sheets

POLYPECTOMY INSTRUMENT

FIELD OF THE INVENTION

The present invention is related in general to medical devices. More specifically, the present invention is related to an instrument for removing polyps.

BACKGROUND OF THE INVENTION

An endoscope is a long flexible tube with a fiber optic light source used to visualize the upper and lower gastrointestinal tract. Such an instrument is often used to search for and remove abnormal growths or polyps from the lining of these organs, particularly the colon. It has been well documented that colon cancer arises in polyps. In populations in which these mushroom-shaped growths have been aggressively sought and removed, the incidence of colon cancer has been reduced. An endoscope is employed to remove polyps with diameters measuring up to approximately one inch; an operation is generally required to extract larger polyps.

There are three basic types of instruments which can be passed down a hollow channel in an endoscope to remove tissue. The first, as shown in FIG. 1a, is a small-cup biopsy forcep. This instrument bites the tissue and is withdrawn into the biopsy channel, pulling with it a small fragment of tissue. While this biopsy forcep can remove very small polyps measuring a few millimeters, it can only biopsy larger lesions. The second instrument, one more suited to the complete removal of the polyp, is the polypectomy snare, as shown in FIGS. 1c and 1d. This is a long thin wire with a lasso at the end contained in a flexible plastic sheath. The endoscopist opens the snare by advancing the wire out of the sheath and closes the snare by pulling the wire back into the sheath. A third type of instrument, as shown in FIG. 1b, is the grasping forcep. The grasping forcep resembles the biopsy forcep in its scissor-like opening and closing action and is usually used to retrieve a polyp after removal.

To perform a polypectomy, the endoscopist advances the scope into the colon until the polyp is well visualized. The snare contained within the plastic sheath is then advanced down the endoscope's biopsy channel. The snare is then opened by advancing the wire through the sheath with a hand-held trigger mechanism. The snare must then be placed over the polyp and gradually tightened around the stalk. As the wire snare is gradually closed, electrical current is passed through the wire, allowing the snare to cut through the stalk in a bloodless fashion. The current is intended to coagulate any small blood vessels in the stalk of the polyp and prevent bleeding. The polyp is then retrieved and sent to the pathologist for evaluation to determine the presence of any cancer therein.

Invariably, the most difficult part of this procedure is getting the snare around the polyp. As one looks down the long tubular colon, the polyp may arise at the three o'clock axis and the snare may exit the endoscope at the nine o'clock axis. With the scope lying within up to six feet of the colon, it is difficult to change the axis. Although the last several centimeters of the scope are very flexible and are manipulated by turning knobs near the eyepiece, placement of the snare over the polyp is often a formidable task.

Another problem encountered during conventional polypectomy is that, once the snare is around the polyp, it is difficult for the endoscopist to tell how close to the wall of the bowel the snare is positioned. Whereas a superficial positioning may result in incomplete removal of a cancerous polyp, an aggressive positioning may cause perforation of the bowel wall with potentially disastrous consequences. Finally, after the stalk is cut, retrieval of the polyp is difficult. Although a grasping forcep can be employed in an attempt to grasp the loose polyp, it is not uncommon for transected polyps to be lost, thus making diagnosis impossible.

The present invention allows a polyp to be grasped so it is not lost when it is separated from the colon, and to be separated from the colon in a safe and effective manner.

SUMMARY OF THE INVENTION

The present invention is an instrument to perform endoscopic polypectomy. The instrument comprises a first portion which grasps a polyp and a second portion which cuts away the polyp. The second portion is in contact with the first portion when the polyp is cut by the second portion while the first portion grasps the polyp. Preferably, the first portion comprises a first sheath member having a small grasping forcep and the second portion comprises a second sheath member having a wire snare. The wire snare is preferably constructed with "memory" so that when it is advanced through the second sheath, it bends toward the first sheath member.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1A:
FIGS. 1a–1d are schematic representations showing prior art instruments.
Figure 1B:
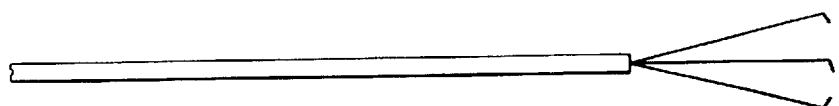
Figure 1C:
Figure 1D:
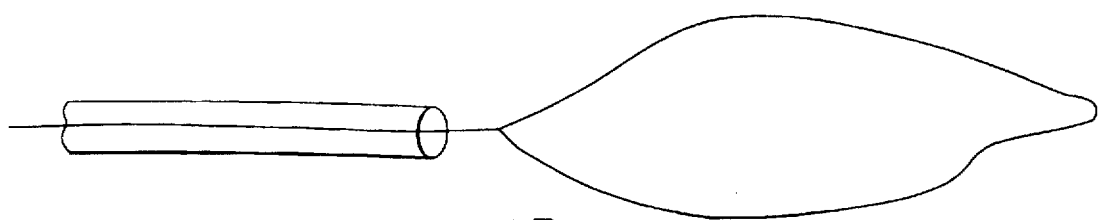
Figure 2A:
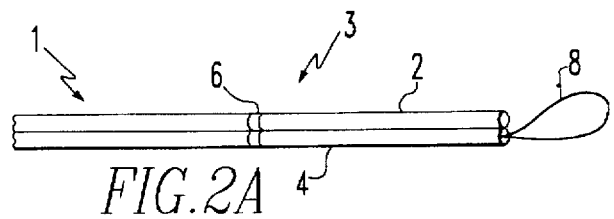
FIGS. 2a–2f are schematic representations illustrating the operation of the instrument.
Figure 2B:
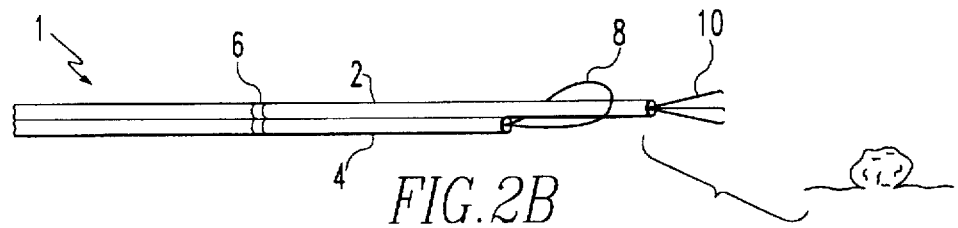
Figure 2C:
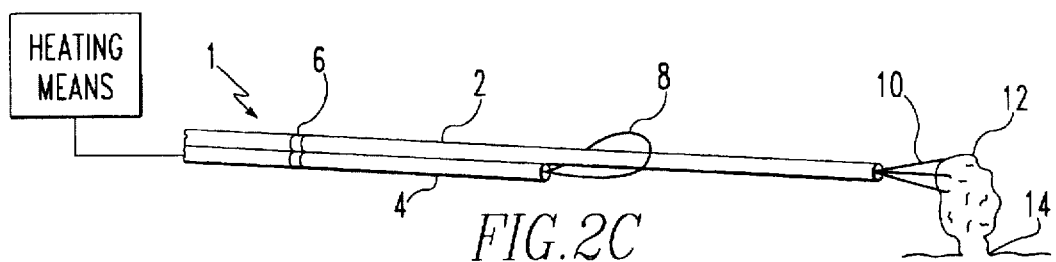
Figure 2D:
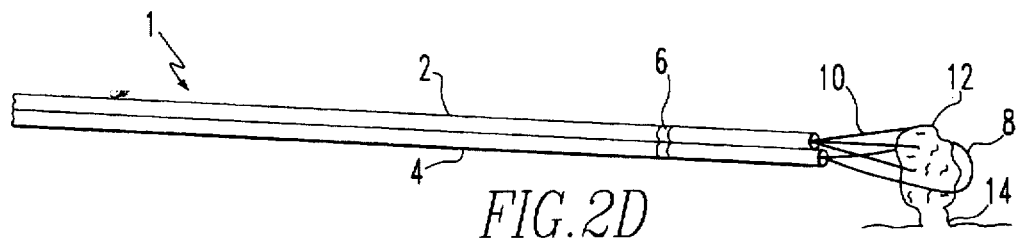
Figure 2E:
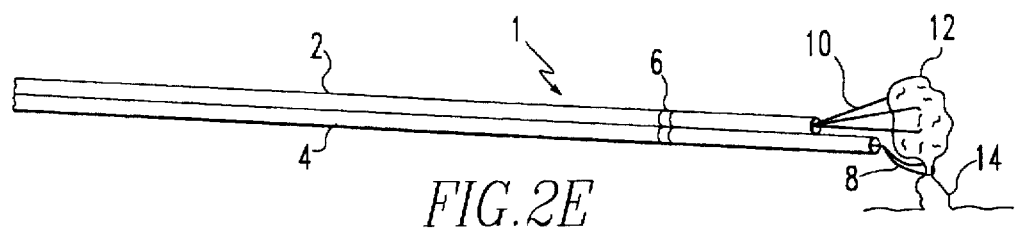
Figure 2F:
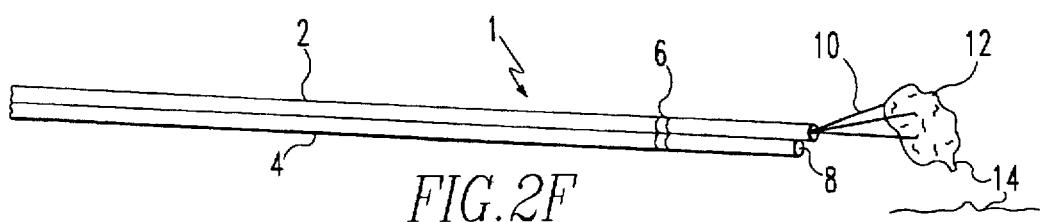

Referring now to the drawings wherein like reference numerals refer to similar or identical parts throughout the several views, and more specifically to FIGS. 2a–2f thereof, there is shown an instrument 1 to perform endoscopic polypectomy. The instrument 1 comprises a first portion which grasps a polyp and a second portion which cuts away the polyp. The second portion is in contact with the first portion when the polyp is cut by the second portion while the first portion grasps the polyp. Preferably, the first portion comprises a sheath member 2 having a small grasping forcep 10, such as that sold by Positrap™ polyp retriever, produced by Microvasive (Boston Scientific Corporation), Watertown, Mass. Preferably, the second portion comprises a sheath member 4 having a wire snare 8 such as that sold by Captivator™ single use polypectomy snare, produced by Microvasive (Boston Scientific Corporation), Watertown, Mass. The wire snare 8 is preferably constructed with memory so that when it is advanced through the sheath member 4, it bends toward sheath member 2 as it opens, as shown in FIG. 2a. As shown in FIG. 2b, the grasping forcep 10 is then advanced through the wire snare 8 to grasp the polyp 12, as shown in FIG. 2c away from the wall of the colon. The wire snare 8 is then advanced over the polyp 12, as shown in FIG. 2d. The polyp 12 can then be pulled with the forcep 10 and cut, as shown in FIG. 2e with the snare 8 at a point just below where the polyp is attached to the colon wall. The snare 8 preferably has an electric current which cauterizes the incision. The polyp 12 can then be removed, as shown in FIG. 2f by maintaining forcep 10 in a grasping position about the severed polyp 12 as the instrument 1 is withdrawn from the colon.

The instrument 1 has at least three very important advantages. First, traction, as shown in FIG. 2e, may be placed on the polyp 12 to pull it away from the wall 14 of the organ, allowing accurate placement of the wire snare 8 under direct visualization with an endoscope to minimize the risks of perforation and incomplete removal of the polyp 12. Secondly, the wire snare 8 is advanced around sheath member 2 so that it must lasso the polyp 12 as it is advanced. This automatic lassoing feature greatly expedites the lassoing of the polyp 12 and makes the entire procedure shorter, safer and less painful with decreased manipulation of the endoscope. Finally, retrieval of the transected polyp 12 is assured by secure purchase of the grasping forceps 12. It should be noted that the size of the diameter of the sheaths 2, 4 must be miniaturized in order to allow passage down a standard endoscope biopsy channel.

In a specific embodiment, sheaths 2, 4 are comprised of silastic and have an outer diameter suitable to fit down the biopsy channel. The channel typically measures about 3.2 mm but most of the instruments are about 2.3 mm. The sheaths 2, 4 have a combined outer diameter of preferably 2.5 mm. The sheath members 2, 4 are connected with a connecting member 6 which allow the sheath members 2, 4 to slide relative to each other during operation. The connecting member 8 preferably has the form of a FIG. 8, with the sheath members inserted through the respective loop of the 8. The connecting member can be made of plastic with the loops forming a tight fit with the members to maintain them in secure relation so they do not wiggle in the loops of the connecting member 6, but such that they can slide in the loops. Preferably, the connecting member 6 is fixed to the first sheath member 2 but in sliding contact with the second sheath member 4, so the second sheath member 4 can be advanced to allow the snare 8 to be placed about the polyp 12 at the proper time.

In the operation of the preferred embodiment, an instrument 10 intended for endoscopic removal of intestinal polyps is comprised of a grasping type forcep 10 and a snare 8 juxtaposed and designed to work in concert with the grasping forcep 10. There are two side-by-side sheaths 2, 4, which, although mechanically coupled, have some ability to slide along each other. These sheaths may be configured so that the contour of each is semi-circular and together the contours form a round cylinder. The first sheath 2 contains a grasping forcep 10 and a second sheath 4 contains a snare 8. This instrument 10 is placed down the hollow channel in the endoscope and advanced to the area of the colon containing the polyp 12. With the polyp 12 in view, the snare 8 is partially advanced from its sheath 4. The wire of the snare 8 is constructed with a "memory" so that as it is advanced, it opens and bends toward the first sheath 2 containing the grasping forcep 10. The grasping forcep 10 is then advanced to the polyp 12 and opened and the polyp 12 is grasped. With the grasping forcep 10 in place and engaged with the polyp 12, gentle traction is placed on the polyp 12. This serves to distract the polyp 12 away from the wall of the intestine 14 and elongate the stalk of the polyp 12. The grasping forcep 10 now acts as a "post" to direct the snare 8 to and over the polyp 12. With the grasping forcep 10 in place, the snare 4 cannot miss the polyp 12. The traction and elongation of the stalk allow for precise placement of the snare around the stalk of the polyp 12 with much better visualization. As the snare 8 is gradually tightened around the stalk of the polyp 12 electrical current is passed through the wire as described above. When the snare 8 has completely cut through the stalk of the polyp 12, the grasping forcep 10 remains firmly attached to the polyp 12. This ensures removal of the polyp 12 and prevents the loss of a loose polyp 12. The endoscope and the instrument 10 are removed from the intestine as a unit and the polyp 12 is sent for pathologic examination. A thin colored stripe is placed along the side of each of the sheaths 2, 4 so that if the endoscopist wishes to change the orientation of the instrument 10, it can be withdrawn from the scope and replaced in a different orientation.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A cut and retrieval instrument comprising:

a first portion which is adapted to grasp a polyp, said first portion includes a first sheath member having a grasping forcep slidably disposed within said first sheath member; and a second portion which is adapted to cut away the polyp, said second portion connected to the first portion, said second portion includes a second sheath member disposed adjacent to the first sheath member having a wire snare with a snare loop slidably disposed within said second sheath member such that the grasping forcep can slide relative to the first sheath member through the snare loop of the wire snare when the snare loop extends from the second sheath member, said loop trained into a bent configuration which upon its advancement out of the second sheath bends towards the forcep so the forcep slides through the loop.

2. An instrument as described in claim 1 wherein the snare loop is comprised of a material having shape memory so as the snare loop bends towards the first sheath member the grasping forcep can slide relative to the first sheath member through the snare loop of the wire snare when the snare loop extends from the second sheath member.

3. An instrument as described in claim 2 wherein the wire snare includes means for heating the snare loop.

4. An instrument as described in claim 3 including a connector member slidably connecting the first sheath member to the second sheath member to allow the first sheath member to slide relative to the second sheath member.

5. An instrument as described in claim 3 wherein the first and second sheath members define an envelope which has a maximum outer dimension less than 1 inch to fit into an endoscope biopsy channel.

6. A method for removing a polyp from a wall of a colon comprising the steps of:

grasping the polyp with a forcep housed in a first sheath member;

pulling the polyp so it moves away from the colon wall;

moving a wire snare over the forcep grasping the polyp until the wire snare is essentially below the polyp and above the colon wall;

closing the wire snare until the polyp is cut from the colon wall; and removing the forcep grasping the polyp from the colon.

\* \* \* \* \*